United States Patent [19]
Surmatis

[11] 3,985,734
[45] Oct. 12, 1976

[54] METHOD FOR THE PREPARATION OF THE COPPER COMPLEX OF 6-METHOXY-1-PHENAZINOL 5,10-DIOXIDE

[75] Inventor: Joseph Donald Surmatis, West Caldwell, N.J.

[73] Assignee: Hoffmann-La Roche Inc., Nutley, N.J.

[22] Filed: Feb. 13, 1974

[21] Appl. No.: 442,297

Related U.S. Application Data

[63] Continuation of Ser. No. 226,305, Feb. 14, 1972, abandoned, which is a continuation-in-part of Ser. No. 139,288, April 23, 1971, abandoned.

[52] U.S. Cl. .............................. 260/242; 424/245; 260/267
[51] Int. Cl.² ....................................... C07D 241/46
[58] Field of Search ................................. 260/242

[56] References Cited
UNITED STATES PATENTS
3,586,674   6/1971   Leimgruber et al. ............... 260/242

OTHER PUBLICATIONS
Hall et al., *J. Chem. Soc.* (London) pp. 425–430 (1965).
McKinnon et al., *J. Chem. Soc.* (London) pp. 3290–3294 (1964).
Cotton et al., *Advanced Inorganic Chemistry*, p. 757 (1962).
Kidani, *Chem. & Pharmaceutical Bull.* (Tokyo) vol. 6, pp. 556–562 (1958).

*Primary Examiner*—John D. Randolph
*Attorney, Agent, or Firm*—Samuel L. Welt; Bernard S. Leon; William M. Farley

[57] ABSTRACT

An improved procedure is described for the preparation of the copper complex of 6-methoxy-1-phenazinol 5,10-dioxide using water as the reaction medium to produce a high yield of free-flowing, crystalline product.

4 Claims, No Drawings

METHOD FOR THE PREPARATION OF THE COPPER COMPLEX OF 6-METHOXY-1-PHENAZINOL 5,10-DIOXIDE

RELATED APPLICATION

This is a continuation of application Ser. No. 226,305, filed Feb. 14, 1972 which is, in turn, a continuation-in-part of prior U.S. patent application Ser. No. 139,288 filed Apr. 23, 1971 both now abandoned.

BACKGROUND OF THE INVENTION

Heretofore, the copper complex of 6-methoxy-1-phenazinol 5,10-dioxide was prepared by combining a saturated solution of 6-methoxy-1-phenazinol 5,10-dioxide (myxin) in a suitable organic solvent with a saturated solution of a copper II salt in the same solvent. Organic solvents which have been employed include acetic acid, acetonitrile, methanol, ether, chloroform etc. The precursor, 6-methoxy-1-phenazinol 5,10-dioxide, is readily prepared by selective methylation of iodinin (1,6-phenazinol 5,10-dioxide) as, for example, by treating the monosodium salt of iodinin with a methylene agent such as dimethyl sulfate in an inert organic solvent. A solution of the 6-methoxy-1-phenazinol 5,10-dioxide when combined with a solution of a cupric salt, e.g., cupric acetate, forms a copper complex containing one mole of copper for every two moles of 6-methoxy-1-phenazinol 5,10-dioxide. Other suitable cupric salts included those of weak acids having pKa's of about 4.2 or higher, such as propionic or benzoic acids and those of mineral acids, such as cupric sulfate, which must be used in buffered solvent systems to avoid highly acidic conditions.

Since the final product is isolated from the reaction medium by precipitation, it is necessary to utilize a solvent or solvent mixture in which both the 6-methoxy-1-phenzinol 5,10-dioxide and the cupric salt are more soluble than the complex formed by their reaction.

This reaction is carried out at room temperature or at temperatures above room temperature to facilitate solution of the reactants and reduce the rather large amount of solvent needed.

The copper complex prepared by the organic solvent method has 90% of its particles below 10 microns in size and usually below 5 microns with the remaining 10% below 20 microns in size. On standing, however, the particles having a strong tendency to form aggregates of from about 400 to 600 microns in size. In order to provide an increased surface area and to afford sufficient solubility so as to achieve an effective degree of physiological activity in the various pharmaceutical preparation, the copper complex of 6-methoxy-1-phenazinol 5,10-dioxide must have this initial particle size distribution of 5-20 microns. However, since the material is thermal, shock and static-sensitive, the conventional means of deaggregation, e.g., jet milling or attrition, are too hazardous.

The aforesaid method of preparation of the copper complex of 6-methoxy-1-phenazinol 5,10-dioxide (hereinafter referred to as copper myxin) has, as noted above, several serious drawbacks. In the first place, because of the low solubility of myxin in organic solvents, a high solvent volume is required for its complexation. The preferred solvent, acetonitrile, is flammable and its use in conjunction with copper myxin is hazardous. In addition, myxin itself is highly flammable and sensitive to electrostatic discharge. Secondly, the initial copper myxin product is a very fine suspension making both filtration and washings difficult and tedious. Further, copper myxin particles, as noted above, have a very strong tendency to form, on standing, aggregates of from 400 to 600 microns in size, thus reducing their chemotherapeutic suitability. Since the material is ten times as sensitive to impact explosion as TNT, milling or grinding operations are very hazardous procedures.

It is an object of this invention, therefore, to provide a method for the preparation of copper myxin which will overcome the deficiencies and hazards of the previous procedure.

BRIEF SUMMARY OF THE INVENTION

This invention relates to an improved method for the preparation of copper myxin. More specifically, this invention relates to a method for the preparation of copper myxin as a free-flowing crystalline solid using water as the reaction medium.

DETAILED DESCRIPTION OF THE INVENTION

This invention relates to the use of water as the reaction medium in an improved procedure for the preparation of copper myxin. It has been found that the reaction in water of myxin with a cupric salt can go to completion, forming a solid suspension therein. This provides a safe, rapid method for the preparation of copper myxin in which yield as a free-flowing crystalline solid which does not agglomerate on standing. The resulting product is purer than the analogous product prepared using organic solvents and has, based on analytical studies, at least a 10% higher thermal stability.

Chemically, copper can exist in ionized form in two combining states—the reduced state, i.e., cuprous or copper I, having a valence of $+1$ and the oxidized state, i.e., cupric or copper II, having a valence of $+2$.

Since myxin is very slightly soluble in water, myxin crystals are added to water and suspended therein by agitation. Some myxin goes into solution as evidenced by the light pink tinge which appears in the water. While the concentration of myxin is not a critical factor per se, its limiting factor is the resultant increase in viscosity to an unsatisfactorily high level at a concentration of 100 grams per liter or higher. The preferred concentration range is from 8–20 grams of myxin per liter of water.

Any water-soluble cupric salt can be used in this process. However, since in the formation of the metal complex of copper myxin there is also formed the acid corresponding to the anionic moiety of the metal salts and since the metal complex of copper myxin is less stable under strongly acidic conditions, it is preferred to use a metal salt of a weak acid. Examples include the salts of any of the acids having a pKa of about 4.2 or greater. Exemplary acids as the lower alkanoic acids, e.g., acetic, propionic etc., benzoic acid and the like. Preferably, the salt is charged to the water as a solid. While no particular concentration range is needed, the concentration should be such as will provide an excess of the copper salt.

The mole ratio of myxin to the metal salt should be about equimolar with, preferably, a slight excess of the copper salt, e.g., 0.75 moles of myxin per 1.25 moles of the metal salt, to insure reaction of all the myxin present in the aqueous suspension.

The reaction temperature and reaction time are not critical factors. The temperature can range from room temperature (20°–25°C.) up to 90°–95°C. and its selection is based on other considerations such as salt solubility and reaction time. Completeness of reaction is noted by the appearance of a green-black suspension of the copper complex of myxin and the complex absence of any rod specks of myxin therein.

The copper complex of 6-methoxy-1-phenazinol 5,10-dioxide has a high degree and wide spectrum of antimicrobial activity in both in vitro and in vivo topical infections. In particular, the copper complex has demonstrated a high level of activity against a wide variety of both gram positive and gram negative bacteria, fungi, protozoa and helminths. This wide spectrum of antimicrobial activity has manifested itself by the efficacy of the copper complex as a chemotherapeutic agent in combatting topical infections.

The antimicrobial activity of copper myxin, prepared by the method of this invention, is established in vivo against 4 strains of bacteria and in vitro against yeast and fungus infections. The following table shows this antimicrobial efficacy.

ANTIMICROBIAL ACTIVITY OF COPPER MYXIN PREPARED IN WATER

| Organism | In vivo $ED_{50}$, mcg/ml |
|---|---|
| S. agalactiae | 4 |
| S. aureus | >500 |
| E. coli | >500 |
| P. aeruginosa | >500 |

| Organism | In vitro Minimum Inhibitory Concentration, mcg/ml | |
|---|---|---|
| | Static | Cidal |
| C. albicans | 12 | 12 |
| M. canis | 0.8 | 24 |

The following examples illustrate the invention

EXAMPLE 1

To four liters of water, preheated to 50°C., are added 50 grams of 6-methoxy-1-phenazinol 5,10-dioxide and 50 grams of cupric acetate monohydrate. The suspension is heated to 80°C. with agitation and maintained at 75°–80°C. for 2 hours. Heating is stopped but agitation is continued until the reaction temperature drops to 35°C. The product is filtered and washed with water (3 × 100 ml); acetone (3 × 100 ml) and, finally, Skelly B (1 × 500 ml), a petroleum solvent essentially n-hexane with a boiling point of 60°–68°C.

The product, after drying for 1 hour at 50°C. and 0.1 mm and cooling to room temperature, passes through a 20 mesh (U.S.) stainless steel sieve. Drying is continued for 24 hours at 60°C. and 0.1 mm pressure. The product is a greenish-black crystalline powder, yield 55 grams (98%, based on myxin) assaying 99.9% copper myxin.

The particle size range can, of course, be varied based on such factors, as agitation rate and reaction temperature. The range can be from 5 to 50 microns with 15–40 microns the desired range.

Copper myxin prepared using water as the reaction medium is characterized as:
 a. Being unhydrated
 b. Decomposition temperature, °C. = 252.4°C. (based on exotherms from a Differential Scanning calorimeter)
 c. ΔH, decomposition, cal/gram = 220.6
 d. Pertinent absorption bands in the IR spectrum: 1365 cm$^{-1}$ (in Fluorolube); 1059, 776, 578 cm$^{-1}$ (in Nujol).

A sample of copper myxin prepared as described above using water as the reaction medium and a sample prepared by the organic solvent method using acetonitrile were analyzed by Induced Electron Emission Spectroscopy (IEE). The position of an IEE band (in electron volts) for a carbon, oxygen, nitrogen and copper atom in a molecule depends on the chemical environment of the atom. Hence IEE spectroscopy is a measure of chemical structure.

Since the spectra for the atoms in both samples are superimposable within experimental error, the atoms must be in the same chemical environment. Hence, both samples have the same chemical structure. The chemotherapeutic efficacies were evaluated by a comparison of the results of Agar Diffusion studies of cream and ointment formulations containing 0.5% of copper myxin prepared from acetonitrile and water respectively. The ointment formulation consisted of

| Ingredient | grams/100 grams |
|---|---|
| Copper Myxin | 0.51 |
| Cosmetic Liquid 687 light | 7.00 |
| Petrolatum (Ultima White, USP) | 92.49 |

The cream formulation consisted of

| Ingredient | Percent by Weight |
|---|---|
| Stearyl Alcohol | 12.5 |
| Petrolatum (Petrolatum Perfecta) | 10.0 |
| Myrj 52 | 4.0 |
| Propylene Glycol | 12.0 |
| Water | 61.5 |

Cosmetic Liquid 687 light is a highly purified, saturated $C_{12}$–$C_{14}$ branched chain hydrocarbon. Ultima White Petrolatum is a purified petrolatum having a melting point of 130°–140°F., a Saybolt Viscosity at 210°F. of 60–66 and a consistency, determined by penetration at 77°F., of 160–190. Petrolatum Perfecta is a purified mixture of semi-solid hydrocarbons ($C_{20}$–$C_{22}$) from petrolatum, melting point range 38°–50°C. Myrj 52 is a polyoxyethylene glycol emulsifying agent scluble in water and alcohol, insoluble in cottonseed oil and milky in propylene glycol.

Using as the test organism *Staphylococcus aureus* 209, the copper myxin prepared from acetonitrile produced larger zones of inhibition in the agar diffusion test than the copper myxin prepared from water. These results indicate a slower dissolution and diffusion rate for the copper myxin prepared from water which is indicative of a more stable crystal structure. Any difference in activity is attributed to differences in crystalline form since, as determined above by Induced Electron Emission Spectroscopy, the materials have the same chemical structures.

This slower release of the activity is useful in situations where irritation is a problem, e.g., bovine mastitis.

I claim:

1. A solid-state reaction method for the preparation of the cupric complex of 6-methoxy-1-phenazinol 5,10-dioxide which comprises reacting, in a water reaction medium, an agitated suspension of solid 6-methoxy-1-phenazinol 5,10-dioxide crystals with a water-soluble cupric salt.

2. A method as in claim 1 where the water soluble copper salt is cupric acetate monohydrate.

3. A solid state reaction method for the preparation of the cupric complex of 6-methoxy-1-phenazinol 5,10-dioxide which comprises reacting, in water at 75° to 80°C. for 2 hours, an agitated suspension of solid 6-methoxy-1-phenazinol 5,10-dioxide with a water soluble cupric salt, filtering the solid suspension product from the water, and drying the product under reduced pressure at 50°–60°C.

4. The free flowing, non-agglomerated crystalline copper complex of 6-methoxy-1-phenazinol 5,10-dioxide prepared according to the solid state reaction process of claim 1.

* * * * *